(12) United States Patent
Barnicki

(10) Patent No.: US 6,353,121 B1
(45) Date of Patent: Mar. 5, 2002

(54) SEPARATION OF 2,5-DIHYDROFURAN FROM WATER BY EXTRACTIVE DISTILLATION

(75) Inventor: Scott Donald Barnicki, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/791,055

(22) Filed: Feb. 22, 2001

(51) Int. Cl.$^7$ ............................................. C07D 307/26
(52) U.S. Cl. ...................................................... 549/507
(58) Field of Search .......................................... 549/507

(56) References Cited

U.S. PATENT DOCUMENTS

| | | |
|---|---|---|
| 3,165,536 A | 1/1965 | Strohmeyer |
| 3,812,158 A | 5/1974 | Besozzi |
| 4,231,941 A | 11/1980 | Drury |

FOREIGN PATENT DOCUMENTS

| | | |
|---|---|---|
| GB | 510365 | 8/1939 |
| GB | 510949 | 8/1939 |

OTHER PUBLICATIONS

Singh et al, Catalytic Dehydration of 2–Butene–1,4–diol, Ind. Eng. Chem. Prod. Res. Dev., vol. 12, No. 3, 1973, pp. 184–189.

Wankat, Equilibrium Staged Separations, Elsevier Science Publishing Co., Inc., 1988, pp. 309–312.

Kister, Distillation Design, McGraw–Hill, N.Y. (1992), Chapter 6.

Kister, Distillation Design, McGraw–Hill, N.Y. (1992), Chapter 8.

Zudkevitch, Chem. Eng. Comm., 161, (1992), pp. 41–65.

Primary Examiner—Ba K. Trinh
(74) Attorney, Agent, or Firm—Michael J. Blake

(57) ABSTRACT

Disclosed is a process for separating 2,5-dihydrofuran (2,5-DHF) from aqueous solution of 2,5-DHF by extractive distillation using certain organic liquids as the extraction agent.

11 Claims, 1 Drawing Sheet

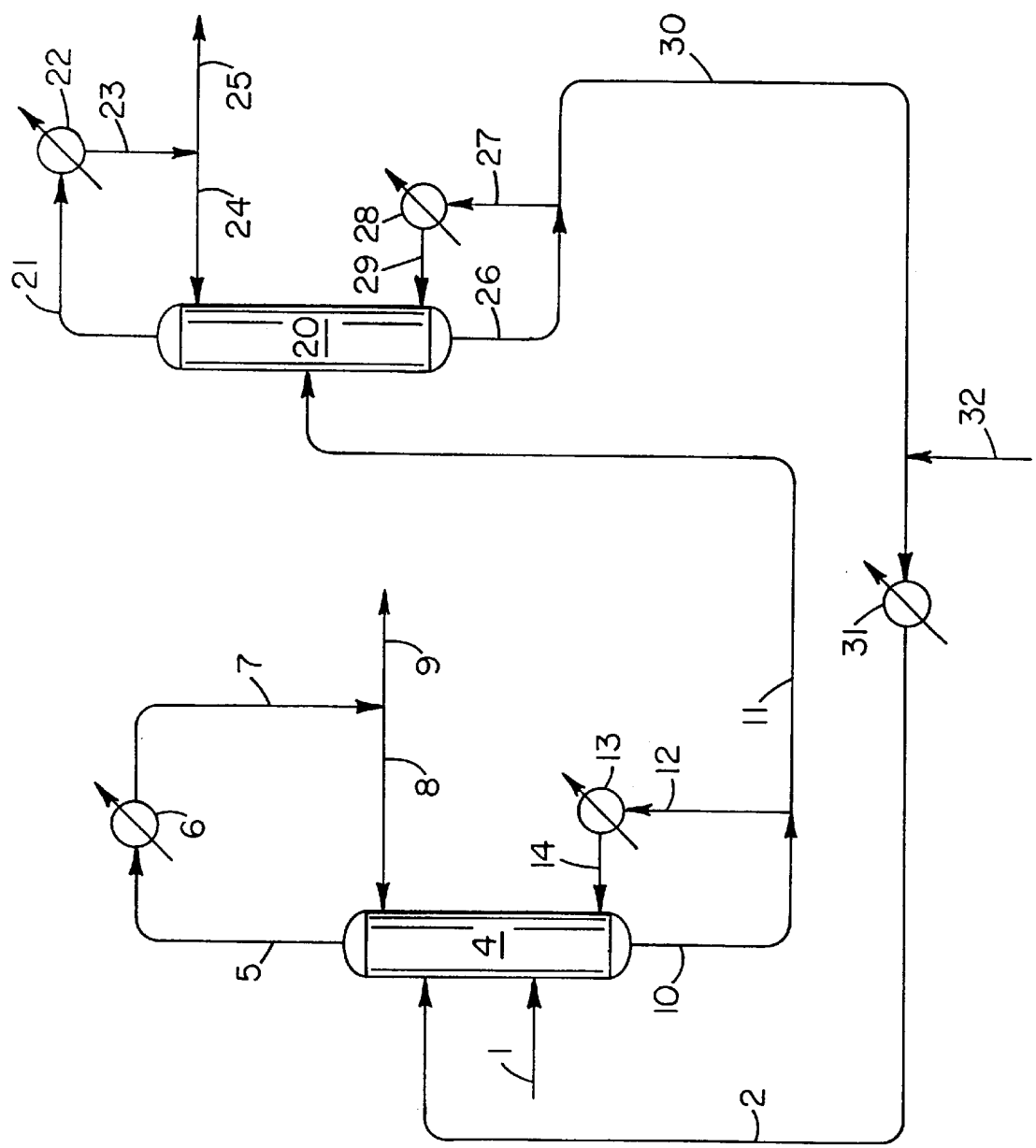

SEPARATION OF 2,5-DIHYDROFURAN FROM WATER BY EXTRACTIVE DISTILLATION

FIELD OF THE INVENTION

This invention relates to a process for separating 2,5-dihydrofuran (2,5-DHF) from aqueous solution of 2,5-DHF by extractive distillation using certain organic liquids as the extraction agent.

BACKGROUND OF THE INVENTION

U.S. Pat. No. 4,231,941 discloses that 2,5-DHF can be synthesized by the simultaneous cyclization and dehydration of 3-butene-1,2-diol (1,2-diol) or 2-butene-1,4-diol (1,4-diol) in a hydroxylic solvent in the presence of solid mercuric oxide. The preferred hydroxylic solvent is water. It is recommended that the 2,5-DHF thus formed be distilled as formed from the reaction mixture as the 2,5-DHF/water minimum-boiling azeotrope.

Similarly, U.S. Pat. No. 3,812,158 discloses that 2,5-DHF can be produced from 1,2-diol or 1,4-diol in a hydroxylic solvent using a soluble mercury salt such as HgSO4. Again, the preferred solvent is water. In the processes described in U.S. Pat. Nos. 3,812,158 and 4,231,941, 2,5-DHF is produced in the presence of large amounts of water as the reaction solvent.

It is known that 1,4-glycols can be dehydrated under acidic conditions to form the corresponding cyclic ether. Such processes are disclosed in U.S. Pat. No. 3,165,536, British Patent 510,949, and Singh, Klinzing, and Coull, Catalytic Dehydration of 2-Butene-1,4-diol, Ind. Eng. Chem. Res. Dev., 12(3), 1973, pages 184–189. Thus, 1,4-diol may be converted to 2,5-DHF by dehydration in either a liquid or vapor phase reaction in the presence of a heterogeneous or a homogeneous acidic catalyst, e.g, sulfuric acid, aluminum oxide, and montmorillonite. Although water-free 1,4-diol can be used as the starting material, the ring closure of the 1,4-diol produces one mole of water for each mole of 2,5-DHF formed. In fact, U.S. Pat. No. 3,165,536 and British Patent 510,949 teach that the 2,5-DHF produced therein is removed continuously from the reaction mixture as the 2,5-DHF/water azeotrope.

In all of the processes cited herein above, the presence of water in the reaction mixture, either as solvent or reaction by-product, cannot be avoided. Thus, any method for the recovery of pure 2,5-DHF from such a reactor effluent must be capable of separating water from 2,5-DHF. None of the patents cited herein provide for a means of obtaining water-free 2,5-DHF in a practical and economical manner on an industrial scale.

U.S. Pat. No. 3,165,536 and British Patent 510,949 disclose that the 2,5-DHF/water azeotrope may be dehydrated with the aid of drying agents such as calcium chloride or potassium carbonate. Although an acceptable drying method in the laboratory, use of a solid drying agent is impractical and not economically practical on an industrial scale. The drying agent is expensive, has low capacity for water, and is difficult to reuse, as the water bound therein to the solid drying agent can be removed only by high temperature treatment.

U.S. Pat. No. 3,165,536 and British Patent 510,949 further disclose that the 2,5-DHF/water azeotrope may be dried by an unspecified azeotropic distillation process. It is well known in the art that 2,5-DHF and water form a minimum-boiling azeotrope with a composition of about 81 mole percent 2,5-DHF and a boiling point of about 63° C. at 760 torr. Although 2,5-DHF and water are only partially miscible, the composition of the azeotrope is outside of the two-phase liquid region at convenient temperatures, e.g., between the freezing point of water and the boiling point of 2,5-DHF. Thus, 2,5-DHF/water solutions cannot be dehydrated to low levels of water by conventional azeotropic distillation techniques employing a dual-column/decanter distillation scheme. An example of such an azeotropic distillation is the dehydration of n-butanol as taught by Wankat in *Equilibrium Staged Separations*, Elsevier Science Publishing Co., 1988, pages 309–312.

Extractive distillation is a method of separating close boiling or azeotrope-forming compounds from each other by carrying out the distillation in a multi-stage rectification column in the presence of an added liquid or mixture of liquids, wherein the liquid(s) have a boiling point higher than the compounds to be separated. The extractive agent is introduced near the top of the column and flows downward to the stillpot or reboiler. Its presence at all points in the liquid phase in the rectification column alters the liquid-phase behavior, and thus the relative volatility of the azeotrope-forming compounds in a manner such that a greater degree of separation than the composition of the azeotrope is possible. The extractive distillation agent should boil higher, usually substantially higher, than any of the azeotrope-forming compounds to be separated. This ensures that the extractive distillation agent remains largely in the liquid phase throughout the column. Usually the extractive agent is introduced a few stages from the top of the column to ensure that the extractive agent is not carried into the distillate with the more volatile component. In order to make subsequent recovery of the extractive agent from the less volatile component of the azeotropic mixture easier and to avoid carry-over of the extractive agent into the distillate, usually it is desirable that the extractive agent does not form azeotropes, either maximum or minimum-boiling, with any of the compounds to be separated. These criteria usually require that the extractive agent boil about 20° C. or more above the boiling point of the lowest boiling azeotrope.

At the bottom of a continuous column, the less volatile component of the azeotropic mixture and the extractive agent are continuously removed from the column. The usual methods of separation of these two components are by a second distillation step, cooling and phase separation, or solvent extraction. For extractive distillation to be an attractive method for separating 2,5-DHF and water, an extractive distillation solvent must (1) create in their presence a large relative volatility between 2,5-DHF and water, and (2) be easy to recover from 2,5-DHF or water.

The usual method of evaluating the effectiveness of extractive distillation agents is to measure the change in relative volatility of the components to be separated in the presence of the candidate agent. Table 1 shows the degree of separation or purity obtainable by theoretical equilibrium stages at several relative volatilities. Table 1 shows that a relative volatility of at least 1.2 is required to get an effective separation by distillation. As the relative volatility is decreased below about 1.2, the number of stages required to effect the separation becomes exponentially larger and the resultant column cost is usually uneconomical. In Table I, Purity is the degree of separation or purity of both products (mole fraction).

TABLE I

EFFECT OF RELATIVE VOLATILITY ON THEORETICAL STAGE REQUIREMENTS

| Relative Volatility: | Theoretical Stages at Total Reflux at Varying Relative Volatilities | | | | | | | |
|---|---|---|---|---|---|---|---|---|
| Purity | 1.00 | 1.02 | 1.1 | 1.2 | 1.4 | 1.5 | 2.0 | 3.0 |
| 0.999 | ∞ | 697 | 144 | 75 | 40 | 33 | 19 | 12 |
| 0.995 | ∞ | 534 | 110 | 57 | 30 | 25 | 14 | 9 |
| 0.990 | ∞ | 463 | 95 | 49 | 26 | 22 | 12 | 7 |
| 0.98 | ∞ | 392 | 81 | 42 | 22 | 18 | 10 | 6 |
| 0.95 | ∞ | 296 | 61 | 31 | 16 | 14 | 8 | 4 |
| 0.90 | ∞ | 221 | 45 | 23 | 12 | 10 | 5 | 3 |

SUMMARY OF THE INVENTION

I have developed a process or method of extractive distillation wherein the relative volatility between 2,5-DHF and water is enhanced to improve the rectification efficiency over that of a single-feed distillation column or reactive distillation column. The present invention provides a extractive distillation process for recovering 2,5-DHF from a mixture comprising 2,5-DHF and water which comprises the steps of:

(1) feeding a mixture comprising 2,5-DHF and water to the mid- or lower section of a distillation column;

(2) feeding an extractive distillation solvent to the upper section of the distillation column;

(3) removing from the upper section or top of the distillation column a vapor comprising 2,5-DHF; and (4) removing from the lower section or bottom of the distillation column a liquid comprising water and the extractive distillation solvent;

wherein the extractive distillation solvent (i) is inert (non-reactive) under the distillation conditions, (ii) does not form an azeotrope with 2,5-DHF and/or water, (iii) is miscible with 2,5-DHF and water, (iv) has a boiling point of at least about 120° at 760 torr. Suitable extractive distillation solvents are stable, can be separated from water or 2,5-DHF and recycled to the extractive distillation column with little decomposition, and create a large relative volatility difference between 2,5-DHF and water in their presence.

BRIEF DESCRIPTION OF THE DRAWING

The accompanying FIGURE is a process flow diagram illustrating a system embodying the principles of the present invention for separating 2,5-DHF and water. While the invention is susceptible to embodiment in various forms, there is shown in the accompanying FIGURE and hereinafter described in detail a preferred embodiment of the invention. The present disclosure is to be considered as an exemplification of the invention without limitation to the specific embodiment illustrated.

DETAILED DESCRIPTION

Relative volatility, α, is defined as the ratio of the equilibrium vapor and liquid compositions of the two components to be separated. Thus, $$\alpha = \frac{\frac{y_1}{x_1}}{\frac{y_2}{x_2}} \quad (1)$$

where $y_i$ is the mole fraction of component i in the vapor phase and $x_i$ is the mole fraction of the component i in the liquid phase. The normal convention in the art is to define the lower boiling pure component as component 1 and the higher boiling pure component as component 2.

In an azeotropic system, the relative volatility will vary from greater than unity to less than unity as one passes through the azeotropic composition. At mole fractions of the lowest boiling component less than the azeotropic composition the relative volatility is greater than unity, while at mole fractions greater than the azeotropic composition the relative volatility is less than unity.

In the convention used herein throughout, relative volatility is taken as the ratio of the equilibrium vapor and liquid mole fractions of 2,5-DHF over the ratio of the equilibrium vapor and liquid mole fractions of water. For the system 2,5-DHF and water, 2,5-DHF is the more volatile component for compositions on the water-rich side of the azeotrope and the relative volatility is greater than unity. On the 2,5-DHF rich side of the azeotrope, water is actually the more volatile component and the relative volatility is less than unity.

At the azeotropic composition, the relative volatility of the components forming the azeotrope is unity. In other words the vapor and liquid compositions are identical. Since distillation works by differences in vapor and liquid compositions, no further separation is possible by simple distillation once the azeotropic composition is reached, even with an infinite number of equilibrium stages.

The process of the present invention may be used in combination with any process wherein a mixture of 2,5-DHF and water are generated. The cyclization and dehydration processes described in U.S. Pat. Nos. 4,231,941, 3,812,158, and 3,165,536 and British Patent 510,365 are typical of processes that produce a reaction effluent that may be employed in the present invention. The pressures referred to herein are given in bars absolute (bara). Herein the terms extractive distillation agent and solvent are used interchangeably.

With reference to the FIGURE, a 2,5-DHF/water feed mixture is fed via line 1 to the middle section of extractive distillation column 4, preferably at least four theoretical equilibrium stages above the bottom of column 4. The feed comprises 2,5-DHF and water as majority constituents. The 2,5-DHF/water mixtures and reaction effluent mixtures suitably employed in this invention may comprise any ratio of 2,5-DHF to water, i.e., from about 0.1 to about 99.9 mole percent 2,5-DHF and 0.1 to 99.9 mole percent water. Preferably the feed to this invention is preconcentrated to approximately the 2,5-DHF/water azeotropic composition, e.g., about 93.5 weight percent 2,5-DHF, for operation at 1.2 bara pressure, before use.

In accordance with the present invention, an extractive distillation solvent is fed to the upper section of the extractive distillation column 4 via line 2, above the feed point of stream 1 and a few stages from the top of column 4. The solvent stream 2 preferably is fed at least 2 theoretical equilibrium stages from the top of distillation column 4. The section above the feed stream 2 serves as a rectifying section to keep the solvent out of the distillate. Preferably the section of column 4 between feed stream 1 and feed stream 2 comprises at least 3 theoretical equilibrium stages, more preferably 5 to 35 stages. The preferred number of total theoretical equilibrium stages in column 4 is 7 to 50 stages, more preferably 10 to 25 stages. The temperature of the solvent feed 2 is in the range of about 0 to 100° C., more preferably about 20° C. to 70° C.

Suitable extractive distillation solvents include, but are not limited to $C_2$ to $C_8$ diols, $C_3$ to $C_{10}$ triols ethers, $C_3$ to $C_{10}$ glycol ethers and glycol ether alcohols; $C_2$ to $C_6$ primary aminoalcohols; $C_4$ to $C_{12}$ secondary aminoalcohols; and polar aprotic solvents including $C_2$ to $C_{10}$ cyclic and acyclic amides, lactams, and sulfoxides. Specific examples of suitable solvents include, but are not limited to, ethylene glycol, 1,2-propylene glycol, 1,3-propylene glycol, 3-butene-1,2-diol (1,2-diol), 2-butene-1,4-diol (1,4-diol), 1,2-butanediol, 1,3-butanediol, 1,4-butanediol, 1-methyl-2-pyrrolidinone (NMP), dimethylformamide, dimethylacetamide, diethylformamide, diethylacetamide, dimethylsulphoxide, morpholine, diethylene glycol dimethyl ether, triethylene glycol dimethyl ether, tetraethylene glycol dimethyl ether, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether, ethanolamine, diethanolamine, 2-amino-1-propanol. The preferred solvents are $C_2$ to $C_4$ diols, more preferably 1,2-diol, 1,4-diol, ethylene glycol, and 1,2-propylene glycol.

The amount of extractive distillation solvent fed to column 4 can vary substantially depending on, for example, the particular vessel configuration, the use of packing material and its type, and the feed rate and composition of stream 1. Generally, the mass ratio of the solvent feed via line 2 to 2,5-DHF/water feed mixture via line 1 is in the range of about 10:1 to about 1:3, more typically about 5:1 to 1:1. Generally, higher concentrations of water in the feed mixture require the use of larger amounts of solvent.

The conditions employed within the extractive distillation column 4 can vary depending on the particular apparatus and solvent employed. The temperature at the top stage of the column is normally from about 60 to 120° C., depending the operating pressure of the column. Boilup, i.e., the heat required to operate the column, is provided to column 4 by reboiler 13. The operating temperature of reboiler 13 normally is within the range of about 100 to 200° C., preferably from about 100 to 160° C. The operating pressure of column 4 is normally within the range of about 0.1 to about 4 bara, and preferably from about 0.8 to 2.0 bara.

A vaporous distillate product is removed from the top of column 4 via line 5 and is cooled in condenser 6 by indirect contact with any typical cooling media such as cooling water, chilled brine, or glycol. A portion of the condensed overhead vapors comprising dehydrated 2,5-DHF is conveyed via conduits 7 and 8 as reflux to the upper section of column 4. A second portion of the dehydrated 2,5-DHF liquid is removed from the system via line 9, e.g., to product storage. The dehydrated 2,5-DHF product of stream 9 typically comprises less than about 1 weight percent water, more typically less than 0.5 weight percent water. The preferred reflux ratio is between 0.5 to 5, more preferably 1 to 2.5, and is adjusted to give a dehydrated 2,5-DHF product having a predetermined composition.

A liquid comprising solvent and water is removed from the bottom of the extractive distillation column via line 10 and is fed via line 11 to a solvent recovery column, described in greater detail below, wherein water is substantially separated from the accompanying solvent for recycle to column 4. A portion of the column underflow is diverted through line 12 to reboiler 13 and the heated liquid is returned to the lower section or base of column 4 through conduit 14.

The solvent-water mixture from the bottom of column 4 is conveyed via lines 10 and 11 to solvent recovery distillation column 20, wherein water is removed from the extractive distillation solvent. The process of the present invention, therefore, may includes the steps of:

(5) feeding the liquid comprising water and the extractive distillation solvent removed from the lower section or bottom of the distillation column in step (4) to the mid-section of a solvent recovery distillation column;

(6) removing from the upper section or top of the solvent recovery distillation column a vaporous distillate product comprising greater than about 99.5 weight percent water; and (7) removing from the lower section or bottom of the solvent recovery distillation column a liquid comprising the extractive distillation solvent.

Stream 11 is fed near the middle, e.g., about half way from the top, of column 20. The preferred number of theoretical equilibrium stages in column 20 is 3 to 20 stages, preferably 5 to 12 stages. The conditions employed within the solvent recovery column 20 can vary depending on the particular apparatus employed. The temperature at the top stage of column 20 normally is from about 40 to 110° C., depending on the operating pressure of the column. Boilup is provided to column 20 by reboiler 28. The operating temperature provided by reboiler 28 at the lower section or bottom of the solvent recovery column normally is within the range of about 100 to 240° C., preferably from about 100 to 180° C. The operating pressure of distillation column 20 is normally within the range of about 0.1 to about 1 bara, and preferably from about 0.15 to about 0.6 bara. Temperatures, pressures, and boilup rate are adjusted such that the liquid solvent stream removed from the bottom of column 20 through line 26 comprises the extractive distillation solvent containing less than 0.5 weight percent, preferably less than 0.2 weight percent, water.

A vaporous distillate product is removed from the top of column 20 via line 21 and is cooled in condenser 22 by indirect contact with any typical cooling media such as cooling water, chilled brine, or glycol. A portion of the condensed overhead vapors, typically comprising greater than 99.5 weight percent water, are conveyed via conduits 23 and 24 as reflux to the upper section of column 20. A second portion of the condensed liquid is removed from the system via conduit 25 for waste disposal. The preferred reflux ratio is between 0.5 to 8, more preferably 1.5 to 5.

The liquid solvent stream removed from the bottom of column 20 through line 26 is returned to extractive distillation column 4 via line 30, heat exchanger 31 and line 2. This liquid stream typically comprises at least 99.5 weight percent, preferably at least 99.8 weight percent, extractive distillation solvent. A portion of the column underflow is diverted through line 27 to reboiler 28 and the heated liquid is returned to the lower section or base of column 20 through conduit 29. Stream 30 may be heat-interchanged with stream 11 to improve the energy efficiency of the process. Make-up solvent may be supplied via line 32. The temperature of stream 30 may be further adjusted by trim heat exchanger 31 to give the desired temperature of the solvent feed 2 in the range of about 0 to 100° C., more preferably about 20C to 70° C.

The extractive distillation column 4 and solvent recovery column 20 typically comprise columnar, pressure vessels containing trays or a packing material that facilitates intimate gas/liquid contact. The gas/liquid contacting equipment in the columns may include, but is not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Palle® rings, and Nutter Rings™. These and other types of suitable gas/liquid contacting equipment are described in detail in Kister, H. Z. Distillation Design, McGraw-Hill, N.Y. (1992), Chapters 6 and 8 the disclosures of which are incorporated herein by reference.

EXAMPLES

The operation of our novel process is further illustrated by the following examples. The efficacy of a particular component for altering the relative volatility of a binary azeotropic system under extractive distillation conditions can be determined by comparing the relative volatility of the binary pair at a given composition in the absence of the candidate agent to the relative volatility of the pair in the presence of a high concentration of the candidate agent. Effective extractive agents will significantly alter the relative volatility of the binary system (either up or down).

A standard solution of water and 2,5-DHF was prepared by mixing 144 grams of 2,5-DHF (99.54 weight percent purity) with 4.5 grams of distilled, demineralized water. A portion of this mixture, comprising 97 weight percent 2,5-DHF or a mixture of identical composition was used for all subsequent examples.

Control Example 1

35 grams of the standard 2,5-DHF/water mixture was charged to a miniature circulation-type vapor-liquid equilibrium still as described by Zudkevitch in *Chem. Eng. Comm.*, 116, (1992), pp. 41–65. The system was allowed to reflux for about three and one half hours while approaching equilibrium. A condensed vapor and an undistilled liquid sample were obtained and analyzed by a gas chromatograph (GC) with a thermal conductivity detector. The GC analysis indicated a vapor composition of 11.9 mole percent water, 88.1 mole percent 2,5-DHF; a liquid composition of 7.8 mole percent water, 92.2 mole percent 2,5-DHF. The relative volatility as calculated by equation 1 is 0.63. Since the composition of the mixture is on the 2,5-DHF-rich side of the azeotrope, the relative volatility is less than unity, as expected.

Examples 1–14

Candidate extractive distillation agents were screened in the following fashion. Approximately 15 grams of the standard 2,5-DHF/water mixture along with approximately 20 grams of a candidate extractive distillation agent were charged to the circulation-type equilibrium still used in Control Example 1. The system was allowed to reflux for about three and one half hours while approaching equilibrium. A condensed vapor and a liquid sample were obtained and analyzed by a gas chromatograph (GC) with a thermal conductivity detector. The relative volatility in the presence of the candidate solvent was calculated from the GC composition data. The results of the relative volatility calculations are summarized in Table II for candidate solvent tested. The Relative Volatilities of the water/2,5-DHF azeotrope and a mixture of 97 weight percent 2,5-DHF and 3 weight percent water in the absence of an extractive distillation solvent are 1.0 and 0.63, respectively.

TABLE II

| Example No. | Extractive Distillation Solvent | Relative Volatility |
| --- | --- | --- |
| 1 | 1,2Propanediol | 2.33 |
| 2 | 3-Butene-1,2-diol | 1.97 |
| 3 | 2-Butene-1,4-diol | 1.46 |
| 4 | 1,2-Butenediol | 2.39 |
| 5 | 2,3-Butanediol | 2.56 |
| 6 | 1,4-Butanediol | 2.13 |
| 7 | 2-(2-Propoxyethoxy)ethanol | 1.83 |
| 8 | 2-(2-Methoxyethoxy)ethanol | 2.34 |
| 9 | Ethylene glycol | 2.71 |
| 10 | Glycerol | 1.51 |
| 11 | Ethanolamine | 14.16 |
| 12 | Diethanolamine | 4.09 |
| 13 | 2-Amino-1-propanol | 6.28 |
| 14 | Morpholine | 1.60 |
| 15 | Dimethylformamide | 3.37 |

Example 16

A computer simulation of the process described herein was carried based on experimental vapor-liquid equilibrium measurements using 3-butene-1,2-diol (1,2-diol) as the extractive distillation solvent. Material balances, temperatures, and pressures of selected process streams are given in Table III. All stream numbers given in Tables III refer to designations in the FIGURE. Temperatures are given in degrees centigrade, pressures in bars absolute, and component flow rates in kg/hour. Extractive distillation column 4 contains 20 theoretical equilibrium stages with the solvent feed on stage 4 from the top and the 2,5-DHF/water feed on stage 15. The column is operated at a solvent to feed molar ratio of 2.3 to 1, a reflux ratio of 2.0, and a pressure of 1.3 bar absolute. Solvent recovery column 20 contains seven theoretical equilibrium stages and is operated at a reflux ratio of 4.0 and a pressure of about 0.3 bar absolute.

TABLE III

| Stream Number | Temperature | Pressure | Composition |||
| --- | --- | --- | --- | --- | --- |
| | | | 2,5-DHF | Water | 1,2-diol |
| 1 | 68.6 | 1.20 | 1787.6 | 121.4 | — |
| 2 | 45.0 | 1.45 | 0.001 | 0.4 | 4403.4 |
| 9 | 45.0 | 1.45 | 1778.7 | 0.4 | 8.2 |
| 11 | 137.4 | 1.30 | 8.9 | 121.4 | 4395.2 |
| 25 | 57.4 | 0.24 | 8.9 | 121.4 | 4390.8 |
| 30 | 157.3 | 0.30 | 0.001 | 0.4 | 4390.8 |
| 32 | 45.0 | 1.45 | — | — | 12.6 |

The invention has been described in detail with particular reference to preferred embodiments thereof, but it will be understood that variations and modifications can be effected within the spirit and scope of the invention.

I claim:

1. Process for recovering 2,5-dihydrofuran (2,5-DHF) from a mixture comprising 2,5-DHF and water which comprises the steps of:
   (1) feeding a mixture comprising 2,5-DHF and water to the mid- or lower section of a distillation column;
   (2) feeding an extractive distillation solvent to the upper section of the distillation column;
   (3) removing from the upper section or top of the distillation column a vapor comprising 2,5-DHF; and
   (4) removing from the lower section or bottom of the distillation column a liquid comprising water and the extractive distillation solvent;

wherein the extractive distillation solvent (i) is inert (non-reactive) under the distillation conditions, (ii) does not form an azeotrope with 2,5-DHF and/or water, (iii) is miscible with 2,5-DHF and water, (iv) has a boiling point of at least about 120° at 760 torr.

2. Process according to claim 1 wherein the extractive distillation solvent is selected from $C_2$ to $C_8$ diols, $C_3$ to $C_{10}$ triols ethers, $C_3$ to $C_{10}$ glycol ethers and glycol ether alcohols; $C_2$ to $C_6$ primary aminoalcohols; $C_4$ to $C_{12}$ secondary aminoalcohols; and polar aprotic solvents selected from including $C_2$ to $C_{10}$ cyclic and acyclic amides, lactams, and sulfoxides.

3. Process according to claim 1 wherein the extractive distillation solvent is selected from ethylene glycol, 1,2-propylene glycol, 1,3-propylene glycol, 3-butene-1,2-diol (1,2-diol), 2-butene-1,4-diol (1,4-diol), 1,2-butane-diol, 1,3-butanediol, 1,4-butanediol, 1-methyl-2-pyrrolidinone, dimethylformamide, dimethylacetamide, diethylformamide, diethylacetamide, dimethylsulphoxide, morpholine, diethylene glycol dimethyl ether, triethylene glycol dimethyl ether, tetraethylene glycol dimethyl ether, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether, ethanolamine, diethanolamine, 2-amino-1-propanol.

4. Process according to claim 1 wherein the extractive distillation solvent is selected from 3-butene-1,2-diol, 3-butene-1,4-diol, ethylene glycol, and 1,2-propylene glycol.

5. Process according to claim 1 wherein the mass ratio of extractive distillation solvent feed to 2,5-DHF/water feed is about 10:1 to about 1:3, more preferably about 5:1 to 1:1.

6. Process according to claim 4 wherein the distillation column comprises 7 to 50 theoretical equilibrium stages.

7. Process according to claim 5 wherein the distillation column comprises 10 to 25 theoretical equilibrium stages.

8. Process for recovering 2,5-dihydrofuran (2,5-DHF) from a mixture comprising 2,5-DHF and water which comprises the steps of:

(1) feeding a mixture comprising 2,5-DHF and water to the mid- or lower section of a distillation column;

(2) feeding an extractive distillation solvent selected from 3-butene-1,2-diol, 3-butene-1,4-diol, ethylene glycol, and 1,2-propylene glycol to the upper section of the distillation column;

(3) removing from the upper section or top of the distillation column a vapor comprising 2,5-DHF and less than about 0.5 weight percent water; and (4) removing from the lower section or bottom of the distillation column a liquid comprising water and the extractive distillation solvent;

wherein the distillation column operates at a temperature of about 100 to 200° C. and a pressure of about 0.1 to about 4 bars absolute.

9. Process according to claim 6 wherein the distillation column operates at a temperature of about 100 to 160° C. and a pressure of about 0.8 to about 2.0 bars absolute pressure.

10. Process according to claim 1 which includes the steps of:

(5) feeding the liquid comprising water and the extractive distillation solvent removed from the lower section or bottom of the distillation column in step (4) to the mid-section of a solvent recovery distillation column;

(6) removing from the upper section or top of the solvent recovery distillation column a vaporous distillate product comprising greater than about 99.5 weight percent water; and (7) removing from the lower section or bottom of the solvent recovery distillation column a liquid comprising the extractive distillation solvent.

11. Process according to claim 10 wherein the solvent recovery column comprises 5 to 12 equilibrium stages, the temperature at the top solvent recovery column is about 40 to 110° C., the temperature at the bottom of the solvent recovery column is about 100 to 180° C., and the pressure within the solvent recovery column is about 0.15 to about 0.6 bars absolute.

* * * * *